United States Patent [19]

Oksman et al.

[11] Patent Number: 4,578,359

[45] Date of Patent: Mar. 25, 1986

[54] OCCULT-BLOOD DETECTION

[75] Inventors: Norman H. Oksman, Mount Vernon, N.Y.; Joseph M. Talmage, Landing, N.J.; Henry J. Wells, Beaumont, Tex.

[73] Assignee: Warner-Lambert Company, Morris Plains, N.J.

[21] Appl. No.: 491,008

[22] Filed: May 3, 1983

[51] Int. Cl.[4] .................. G01N 1/02; G01N 33/52; G01N 33/72
[52] U.S. Cl. .................... 436/66; 128/638; 128/759; 422/56; 435/28
[58] Field of Search .............. 128/749, 759, 638; 422/55, 56, 57, 58; 436/66, 169, 170; 435/28; 428/284; 604/361

[56] References Cited

U.S. PATENT DOCUMENTS

| | | | |
|---|---|---|---|
| 3,718,431 | 2/1973 | Wild | 128/749 X |
| 4,082,886 | 4/1978 | Butterworth et al. | 428/284 |
| 4,175,923 | 11/1979 | Friend | 436/66 |
| 4,259,964 | 4/1981 | Levine | 128/759 X |
| 4,273,741 | 6/1981 | Levine | 422/56 |
| 4,333,734 | 6/1982 | Fleisher | 436/66 |
| 4,365,970 | 12/1982 | Lawrence et al. | 436/66 |
| 4,420,353 | 12/1983 | Levine | 422/56 X |

FOREIGN PATENT DOCUMENTS 0901754 6/1972 Canada.
1018563 1/1966 United Kingdom ............ 436/169

OTHER PUBLICATIONS

Rider et al., Journal of the American Medical Association, vol. 56, pp. 31–33, (9/4/54).

Primary Examiner—Barry S. Richman
Assistant Examiner—Robert J. Hill, Jr.
Attorney, Agent, or Firm—Gary M. Nath

[57] ABSTRACT

A specimen-collection wipe 2 is suitable for use in testing for the presence of occult blood in fecal matter or other bodily substance. The wipe 2 includes a substrate 4 having a hand-contact surface 11 for manipulating the wipe 2 and an occult-blood detection-test surface 10 for collecting a specimen and supporting it during treatment with an occult-blood indicator fluid. The substrate 4 has a sufficiently low wet strength to permit the wipe 2 to be disposed of in a toilet and preferably has a sufficiently high resistance to seepage to permit the hand-contact surface 11 to remain dry for the duration of the test. The wipe 2 also includes an indicator-activity verification region 14 on which is dispersed a reagent capable of interacting with the occult-blood indicator fluid to provide an indication characteristic of the presence of occult blood.

11 Claims, 2 Drawing Figures

OCCULT-BLOOD DETECTION

TECHNICAL FIELD

The present invention relates to a disposable wipe for use in collecting specimens of fecal matter or other bodily substance and testing the specimens for the presence of occult blood.

BACKGROUND ART

The presence of blood in feces can signal the existence of a tumor, ulcer, or other medical disorder along the digestive tract. In early stages of development, a tumor or ulcer on the digestive tract may bleed to such a slight extent that the blood, while present in the feces, is not visible. Nonetheless, in such cases, the blood, termed "hidden" or "occult" blood, can usually be detected with one of a number of indicator reagents which change color in the presence of the hemoglobin in blood.

One of the most widely used occult-blood indicator reagents is derived from an extract from the wood of certain species of trees of the Guaiacum genus native to the American tropics. The extract, termed guaiac, turns from essentially colorless to blue in the presence of hemoglobin and an oxidizing agent such as hydrogen peroxide. More specifically, the guaiac reagent is sensitive to what is termed "peroxidase activity" which results from the combination of an oxidizing agent with hemoglobin or certain chemically similar compounds.

Testing feces for the presence of occult blood with an occult-blood indicator reagent is a valuable medical diagnostic tool, since such testing can often detect tumors in the digestive tract at an early stage of their development, typically before the tumors manifest other symptoms and at a stage when they can be treated most successfully.

A procedure widely used by physicians and medical laboratories for testing for occult blood in fecal matter makes use of a test slide of the type disclosed in U.S. Pat. No. 4,365,970 to Lawrence and Townsley. The test slide of the Lawrence and Townsley patent includes a sheet of guaiac-impregnated indicator paper enclosed in a cardboard envelope. A front panel of the envelope has openings in it for smearing samples of fecal matter on a first side of the indicator paper. A rear panel of the envelope has an opening for applying a hydrogen peroxide developing solution to a second side of the indicator paper. A blue stain on the indicator paper signifies the presence of occult blood in the sample of fecal matter on the opposite side. Since the blue stain appears on the side of the indicator paper opposite to the samples of fecal matter, the developing solution necessarily soaks through the paper in the test procedure. The indicator sheet of the test slide of the Lawrence and Townsley patent has a control area designated on its second side which includes a positive monitor and a negative monitor. Hemin, a hemoglobin-derived compound, is printed on the positive monitor, but not on the negative monitor. Application of the developing solution to the control area causes the indicator paper to turn blue at the positive monitor and remain colorless at the negative monitor if the test reagents are properly active and if the test slide has not been contaminated with a compound which yields a false indication of the presence of hemoglobin.

Although the test slide of the Lawrence and Townsley patent is generally satisfactory for use in a doctor's office or a hospital, it has significant disadvantages for home use. An applicator stick must be used to collect each sample of fecal matter from a toilet bowl and to smear the sample on the test slide. The person using the test slide thus has the problem of disposing of the applicator sticks and, after applying the developing solution to the slide, disposing of the test slide itself. Neither the applicator sticks nor the test slide can be flushed down the toilet. Even if the test slide is forwarded to a doctor's office or medical laboratory for analysis, the problem of disposing of the soiled applicator sticks remains for the user.

U.S. Pat. No. 4,175,923 to Friend discloses a test for the presence of occult blood in fecal matter which is intended to be carried out at home. The test makes use of an indicator paper prepared by impregnating a sheet of absorbent paper with guaiac reagent. A portion of the indicator paper is also impregnated with blood. The test of the Friend patent involves applying a developing solution to a sheet of the indicator paper and then tossing the sheet into a toilet bowl to contact the paper with the water in the bowl. The developing solution causes the portion of the indicator paper impregnated with blood to turn blue if the guaiac reagent and developing solution are properly active. If stools in the toilet bowl contain occult blood, blood will disperse in the water in the bowl. Blood in the water in the toilet bowl will in turn cause the remainder of the indicator paper to turn blue. After allowing time for the color of the indicator paper to change, the paper can be flushed down the toilet with the stools.

Although the occult-blood detection test of the Friend patent is satisfactory in principle, it is limited in a number of respects. Ordinarily, for occult blood in fecal matter to be detected by the test, the blood must disperse in the water of the toilet bowl. Such dispersal necessarily dilutes the blood and thus reduces the sensitivity of the test. In addition, the test results may be suspect as a consequence of the presence of contaminants in the toilet bowl. Furthermore, guaiac reagent is subject to degradation by oxygen in the air. Consequently, the sheets of indicator paper are preferably stored individually in sealed foil envelopes or air-tight packages of some other sort to increase shelf-life stability. Such air-tight packaging increases the cost of the test to the user.

DISCLOSURE OF THE INVENTION

We have invented a convenient disposable specimen-collection wipe for use in an occult-blood detection test suitable for carrying out at home which avoids problems of the prior art noted above. The specimen-collection wipe is especially suited for use in connection with a method and composition for detecting peroxidase activity disclosed in U.S. patent application Ser. No. 471,372, filed Mar. 1, 1983 (the '372 application) and assigned to the assignee of the present application. The specification of the '372 application is hereby incorporated by reference in the present application.

Broadly, the specimen collection wipe of the present invention comprises a substrate having a hand contact surface for manipulating the wipe and an occult-blood detection-test surface. Two regions are defined on the detection-test surface: (1) a specimen-collection region for collecting a specimen of fecal matter or other bodily substance and for supporting the specimen during application of an indicator fluid such as one of the self-developing indicator solutions disclosed in the '372 application cited above, and (2) an indicator-activity verification region for testing the activity of the indicator fluid. The substrate is guaiac free and constructed of a pliable material such as multiple-ply tissue paper. The substrate has a sufficiently low wet strength to permit the wipe to be flushed down a toilet. In addition, the substrate preferably has a sufficiently high resistance to seepage by the indicator fluid from the detection-test surface to the hand-contact surface to permit the hand-contact surface to remain dry for the duration of an occult-blood detection test.

The wipe of the invention incorporates an indicator-activity test reagent in the indicator-activity verification region of the detection-test surface of the substrate. The indicator-activity test reagent is capable of interacting with the indicator fluid to provide an indication characteristic of the presence of occult blood. Thus, if a '372 of a self-developing-guaiac indicator solution of the '372 application is sprayed on the indicator-activity verification region of a wipe of the invention, the indicator fluid ordinarily turns from essentially colorless to blue. Failure of the indicator fluid to change color is a signal that the indicator fluid may be inactive for some reason and that any negative result of the occult-blood detection test should be suspect.

The wipe is of a size and shape to be manipulated by hand and therefore a wide range of sizes and shapes are usable. In a preferred embodiment of the invention, the wipe is in the form of a generally rectangular pad from about 80 mm to about 150 mm wide and from about 100 mm to about 200 mm long. Dimensions of roughly 100 mm wide by roughly 150 mm long are particularly preferred. Alternatively, the wipe could be circular or oval in shape. The wipe could also be fabricated as a mitt to be worn over the hand. It will be recognized that the wipe of the invention could be fabricated in other forms and sizes.

In a preferred embodiment of the invention, the substrate is a generally rectangular pad formed from a number of sheets of absorbent, porous, soft, low-wet-strength paper of the type used as toilet tissue. The sheets are arranged one on top of the other. For example, a pad composed of nine plies of tissue paper has served successfully as a substrate for a wipe of the invention. However, either a greater or lesser number of plies may be advantageous in certain applications, depending, for example, on the weight and stiffness of the individual plies of tissue paper.

In an embodiment in which the substrate is a pad formed from plies of tissue paper, the plies are preferably joined together around their periphery. The plies may be joined by crimping. Crimping the plies together around the periphery of the pad permits the plies to separate from one another readily when the wipe is soaked with water. Consequently, the wipe may be safely disposed of in a toilet. Furthermore, a pad formed from plies of tissue paper crimped together is economical to manufacture. Alternatively, the plies of tissue paper may be joined with an adhesive, preferably applied around the periphery of the pad. The adhesive is preferably water soluble or otherwise water degradable to permit the wipe to be disposed of readily in a toilet.

The wipe of the invention is preferably biodegradable.

The substrate of the wipe of the invention should not include any contaminant in the specimen-collection region which would give rise to a false indication of the presence of occult blood. Commercially available grades of tissue paper such as used for toilet tissue generally do not include such contaminants.

For use with a self-developing guaiac indicator solution of the '372 application, the detection-test surface of a wipe of the invention is advantageously white or yellow in color to provide a visual contrast with the indicator fluid, which turns blue on contact with occult blood. To less advantage, the surface may also be colored pink. A green or blue color for the detection-test surface in this application, while possible, is generally not preferred, since a blue or green background tends to mask the color change provided by the guaiac indicator solution.

The indicator-activity test reagent preferably includes hematin, a derivative of hemoglobin with the following systematic name: [7,12-Diethenyl-3,8,13,17-tetramethyl-21H,23H-porphine-2,18-dipropanoato(2-)-$N^{21},N^{22},N^{23},N^{24}$]-hydroxyiron. Hematin may be applied to the indicator-activity verification region as a basic solution in a mixture of ethanol and water. Any reagent exhibiting peroxidase-like activity; such as hemin, hemoglobin, or whole blood (either human blood or animal blood); may be used as an indicator-activity test reagent if desired since such reagents provide a reaction with indicator fluids characteristic of occult blood.

The indicator-activity verification region is preferably substantially smaller in area than the specimen collection region and is preferably clearly marked on the detection-test surface of the wipe of the invention. The shape of the indicator-activity verification region is not critical. The verification region, for example, may be generally circular, rectangular, or of another shape. More than one indicator-activity verification region may be included if desired. A corresponding region which includes no indicator-activity test reagent may be marked on the detection-test surface as well to serve as a neutral-response region. Ink used for marking the various regions on the detection-test surface should be safe for human contact and should not give rise to a false indication of the presence of occult blood or otherwise distort the results of the test.

Preferably, the substrate of a wipe of the invention retards the seepage of indicator fluid from the detection-test surface of the wipe to the hand-contact surface for at least 30 seconds to give the user time to hold the wipe in his hand and observe the test results before dampness is detected on the hand-contact surface. The hand-contact surface of a preferred wipe of the invention made up of nine plies of tissue paper generally remains dry to the touch indefinitely after a standard occult-blood detection-test dose of roughly 0.9 ml of a self-developing indicator solution of Example I the '372 application is applied to the detection-test surface on the opposite side of the wipe. Although it is possible to soak such a wipe through in less than 30 seconds by applying three times the standard test dose of indicator solution, when the standard test dose is applied, the indicator solution generally evaporates to dryness from the detection-test surface before it can penetrate to the hand-contact surface of the wipe.

It is believed that the remarkable resistance to seepage from front to back in a pad of plies of tissue paper joined at their periphery is a result of the light contact the various plies make with one another in the central region of the pad. Fluid tends to flow by capillary action laterally within a sheet of tissue paper far more readily than it tends to flow from one sheet of tissue paper to the next. Moreover, the first four or five plies or so of the nine plies of tissue paper in preferred wipes of the invention have sufficient fluid-holding capacity to absorb all of the indicator fluid applied to the wipe in a typical occult-blood detection test.

Although in principle a moisture-impermeable polymer film could be incorporated in the wipe of the invention to serve as a moisture barrier, conventional polymer films typically have too great a wet strength to be readily disposable in a toilet.

BRIEF DESCRIPTION OF THE DRAWING

Preferred embodiments of the invention are described below with reference to the following figures.

BEST MODE FOR CARRYING OUT THE INVENTION

Figure 1:
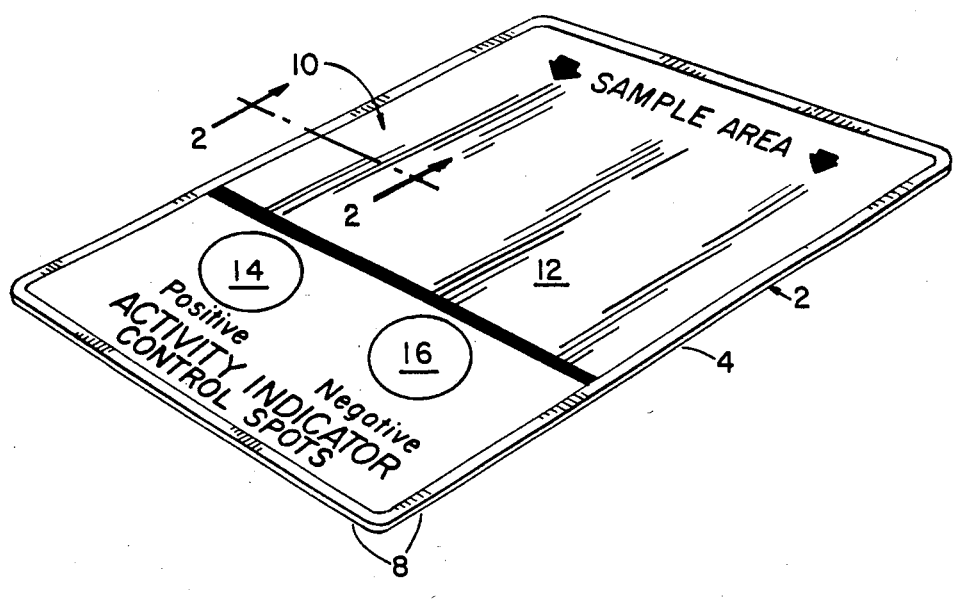
FIG. 1 is an oblique view of a specimen-collection wipe of the present invention.
Figure 2:
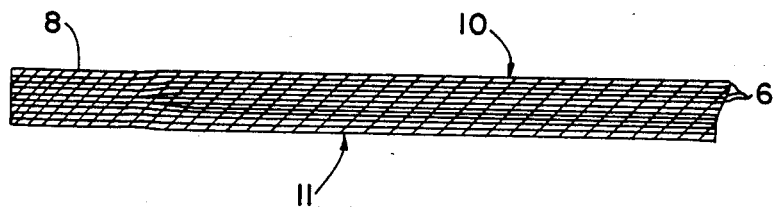
FIG. 2 is a partial crossectional side view of the wipe of FIG. 1 taken along line 2—2.

Turning now to FIG. 1, a specimen-collection wipe 2 includes a pad 4. As shown in FIG. 2, the pad 4 is made up of nine plies of tissue paper 6 arranged one on top of the other. The plies of tissue paper 6 are crimped together around the periphery 8 of the pad 4. A first side 10 of the pad 4 defines an occult-blood detection test surface for the wipe and a second side 11 defines a hand-contact surface. Printed on the detection-test surface 10 are designations of three regions: a specimen collection region 12, a indicator-activity verification region 14 and a neutral-response region 16. The indicator-activity verification region 14 is denoted "Positive" and the neutral-response region 16 is denoted "Negative." A hematin reagent is absorbed in the indicator-activity verification region 14.

The hematin reagent is deposited within the indicator-activity verification region 14 by moistening the region 14 with a hematin solution, then allowing the solvent to evaporate from the moistened area to leave behind a deposit of hematin reagent. The hematin solution is prepared as follows: Water and ethanol are mixed in the proportion of about 25 percent by volume water and about 75 percent by volume ethanol. Sodium hydroxide is added to the water/ethanol mixture in an amount sufficient to form a solution of about 0.01 molar sodium hydroxide. To this basic water/ethanol solution is added a quantity of hematin sufficient to yield a solution containing about 6 mg of hematin per liter of solution.

The self-developing indicator solution of Example II, Run 2 of the '372 application is suitable for use with the wipe 2. This indicator solution may be prepared as follows: To a flask is added about 100 ml of ethanol followed by addition of about 1 gram of guaiac powder. The contents are mixed for approximately 30 minutes to dissolve the guaiac indicator in the ethanol solvent. The solution is filtered to remove undissolved particles. About fifty (50) ml of the resulting solution is mixed with approximately 4.5 ml of about 30 percent hydrogen peroxide, followed by the addition of about 15 ml of approximately 0.1 molar citrate buffer to adjust the pH to about 5.0. Approximately ten (10) ml of water are added to prevent crystallization of the buffer. Fresh ethanol is then added to increase the volume to about 100 ml. The resulting solution exhibits a slight amber color.

The wipe 2 in conjunction with the self-developing indicator solution of the preceding paragraph can be used as follows to test for the presence of occult blood in fecal matter. The user first obtains a sample of fecal matter by defecating. A specimen of the fecal matter is collected on the specimen-collection region 12 of the wipe 2 by contacting the region 12 the wipe 2 with the fecal matter while defecating or by patting in the anal area with the region 12 of the wipe 2. The user then applies a dose of the occult-blood indicator solution from a spray applicator to the specimen of fecal matter on the wipe. Typically, three squirts are applied, with each squirt of the applicator delivering roughly 0.18 ml of solution. In addition, single-squirt doses of indicator solution are applied respectively to the indicator-activity verification region 14 and to the neutral-response region 16 of the wipe. If the indicator solution is properly active, the solution will change color in the indicator-activity verification region 14. If the wipe has not been contaminated with a substance which gives a false indication of occult blood, the indicator solution will remain essentially colorless in the neutral response region 16. Thus, if the indicator solution either fails to turn blue in the indicator-activity verification region 14 or turns blue in the neutral response region 16, the results of the test are suspect. If the indicator solution which contacts the specimen of fecal matter does not change color, the specimen probably contains at most an insignificant quantity of occult blood. If, on the other hand, the indicator solution which contacts the specimen turns blue, the presence of occult blood is indicated and the user should consult a physician. After the test is completed the user can toss the wipe into the toilet bowl and flush it away.

It is not intended to limit the present invention to the specific embodiments described above. For example, the substrate of the wipe of the invention may be made of flushable felt, wadding, sponge or fabric, if desired. A pad suitable for a wipe of the invention may be made from sheets of creped, low-wet-strength tissue. The wipe may be folded so that the indicator-activity verification region and neutral-response region generally face away from the specimen-collection region to prevent the indicator-activity verification and neutral-response regions from becoming soiled with fecal matter during the collection of a specimen. After collection of the specimen, the wipe can be unfolded to permit the indicator fluid to be applied conveniently to all three regions. The indicator-activity verification region and neutral-response region may be covered with a removable, flushable paper strip or other suitable barrier to soiling if desired. The wipe of the invention may be used with indicator fluids other than those disclosed in the '372 application and may be used to detect occult blood in bodily substances other than fecal matter. It is recognized that these and other changes may be made in the invention specifically described herein without departing from the scope and teachings of the instant invention and it is intended to encompass all other embodiments, alternatives, and modifications consistent with the invention.

We claim:

1. A process for testing for occult blood in fecal matter employing an occult blood indicator fluid, the process comprising:

(a) contacting fecal matter or an anal area with a specimen-collection region of a guaiac-free specimen-collection wipe to collect a specimen of fecal matter on the wipe, the wipe being made of a pliable pad comprising a plurality of sheets of absorbant, porous, soft material disposed one on top of another and joined together around their periphery to form a multilayer structure having sufficiently low wet strength to permit the wipe to be disposed of in a toilet, said pad including a first outermost sheet providing an occult-blood detection-test surface and a second outermost sheet providing a hand-contact surface, a first area of said occult-blood detection-test surface being said specimen-collection region and a second area of said occult-blood detection-test surface being an indicator-activity verification region, said indicator-activity verification region having an indicator-activity test reagent therein, and said indicator-activity test reagent being capable of interacting with an occult-blood indicator fluid to provide a color indication when the occult-blood indicator fluid is sufficiently active to provide a color in the presence of occult blood;

(b) applying an amount of an occult-blood indicator fluid to the indicator-activity verification region of the wipe and observing any change in color after a predetermined period of time to verify whether or not the occult-blood indicator fluid is sufficiently active to provide a color in the presence of occult blood;

(c) applying an amount of the occult-blood indicator fluid of step (b) to the specimen of fecal matter on the speciman-collection region of the wipe at about the same time as applying the occult-blood indicator fluid to the indicator-activity verification region and observing any change in color after said predetermined period of time to determine if the fecal matter contains occult blood, providing that the occult-blood indicator fluid and the amounts thereof, and the material of construction and number of said sheets of said pad are selected such that the wipe has a sufficiently high resistance to seepage by the occult-blood indicator fluid applied in steps (b) and (c) to permit the hand-contact surface of the wipe to remain dry during said predetermined period of time; and (d) flushing the entire wipe down a toilet to dispose of the wipe.

2. The process of claim 1 in which the indicator-activity-test reagent includes hematin.

3. The process of claim 1 in which the amounts of occult-blood indicator fluid are applied by a spray applicator.

4. The process of claim 1 in which the sheets are paper.

5. The process of claim 4 in which the sheets are tissue paper.

6. The process of claim 5 in which the sheets of tissue paper are joined together around their periphery by crimping.

7. The process of claim 5 in which the sheets of tissue paper are joined together around their periphery by a water-degradable adhesive.

8. The process of claim 5 in which the pad comprises nine sheets of tissue paper.

9. The process of claim 1 in which the wipe is a pad generally rectangular in shape.

10. The process of claim 9 in which the area of the indicator-activity verification region is substantially less than the area of the specimen-collection region.

11. The process of claim 10 in which the pad is folded so that the indicator-activity verification region and the specimen collection region face in generally opposing directions during the contacting step.

* * * * *